United States Patent
Godart

(10) Patent No.: US 8,194,891 B2
(45) Date of Patent: Jun. 5, 2012

(54) VOLUME CONTROLLED PRENATAL MUSIC BELT

(76) Inventor: Adrianne Godart, Denver, CO (US)

( * ) Notice: Subject to any disclaimer, the term of this patent is extended or adjusted under 35 U.S.C. 154(b) by 496 days.

(21) Appl. No.: 12/423,533

(22) Filed: Apr. 14, 2009

(65) Prior Publication Data

US 2009/0274323 A1    Nov. 5, 2009

Related U.S. Application Data

(60) Provisional application No. 61/044,650, filed on Apr. 14, 2008.

(51) Int. Cl.
*H03G 3/00* (2006.01)
(52) U.S. Cl. .................. 381/109; 381/124; 434/319
(58) Field of Classification Search ............ 381/109, 381/124; 434/319; 224/224, 664
See application file for complete search history.

(56) References Cited

U.S. PATENT DOCUMENTS

| | | | |
|---|---|---|---|
| 4,798,539 A * | 1/1989 | Henry et al. | .......... 434/319 |
| 4,830,007 A | 5/1989 | Stein | |
| 4,934,998 A | 6/1990 | Thomas, Jr. | |
| 5,109,421 A | 4/1992 | Fox | |
| 5,491,756 A | 2/1996 | Francais | |
| 5,699,558 A | 12/1997 | Min | |
| 5,873,736 A * | 2/1999 | Harrison | .......... 434/322 |
| 5,898,787 A | 4/1999 | Stanford | |
| 5,913,834 A * | 6/1999 | Francais | .......... 600/591 |
| 6,422,242 B1 * | 7/2002 | Slautterback et al. | ...... 128/846 |
| 6,718,044 B1 | 4/2004 | Alleyne | |
| 6,840,775 B2 | 1/2005 | Sailors | |
| 2003/0016840 A1* | 1/2003 | Sica | .......... 381/333 |
| 2004/0180318 A1* | 9/2004 | Sailors | .......... 434/365 |

* cited by examiner

*Primary Examiner* — Phuc Dang
(74) *Attorney, Agent, or Firm* — Marsh Fischmann & Breyfogle LLP

(57) ABSTRACT

The present invention transmits sounds and/or music to an unborn baby in the mother's womb via a waist belt and speaker disposed within the belt, where the speaker connects to most audio devices via a universal audio plug. The waist belt can also be used to temporarily house/transport appropriate portable audio devices in an internal pocket. The speaker of the present invention utilizes a volume control unit that is separate from a volume control of an attached audio device and that allows for limiting and/or adjusting the sound volume delivered by the speaker. The separate volume control unit is an improvement over any previously known devices because it provides additional safety for the developing baby's hearing.

17 Claims, 5 Drawing Sheets

VOLUME CONTROLLED PRENATAL MUSIC BELT

CROSS REFERENCE TO RELATED APPLICATION

This application claims the benefit of the filing date of U.S. Provisional Application No. 61/044650 entitled "VOLUME CONTROLLED PRENATAL MUSIC BELT" having a filing date of Apr. 14, 2008, the entire contents of which are incorporated herein by reference.

BACKGROUND OF THE INVENTION

Resent research has shown that an unborn baby (fetus) has the ability to hear sound while still in the womb. It is further believed that an unborn baby may also recognize and react to certain sounds, such as: music, the mother's and/or father's voice, and a variety of other natural and/or man-made sounds.

The extraordinary benefits of sound and music during pregnancy have been documented over the last twenty years, due to a period of tremendous scientific advancement in our understanding of life in the womb, and its consequences thereafter. It has been established that the baby before birth is a hearing, feeling, and sensing being.

Research has also shown that babies develop prenatal memories. The sounds and/or music that are heard frequently before birth will be recognized after birth. This has been observed as the babies physically turned to the source of the sound or were completely absorbed by the sounds and/or music being played.

Hearing is believed to be the first sense to develop in the embryo, appearing in the third week of gestation. Sound and/or music may have a variety of effects on the unborn fetus, including; fetal development, stimulation, cognitive development, relaxation, musical therapy, baby & mother bonding and enjoyment for both mother and developing baby.

SUMMARY OF THE INVENTION

The present invention transmits sounds and/or music to an unborn baby in the mother's womb via a waist belt and speaker disposed within the belt, where the speaker connects to most audio devices via a universal audio plug. The waist belt can also be used to temporarily house/transport appropriate portable audio devices in an internal pocket. The internal pocket typically includes a means to securely close the pocket. Such means may include, without limitation, zippers, hook and loop fasteners and buttons. Generally, a speaker wire and universal audio plug may extend from the speaker into the internal pocket.

While it is believed that providing sound and music to unborn babies has numerous benefits, the present inventors have recognized it may be desirable to avoid excessive sound levels. Accordingly, the speaker of the present invention utilizes a volume control element/or unit that is separate from a volume control of an attached audio device and that allows for limiting and/or adjusting the sound volume delivered by the speaker. The separate volume control unit is an improvement over any previously known devices because it provides additional safety for the developing baby's hearing. The volume control unit may be disposed between the speaker and the universal plug or integrated into the speaker.

As will be appreciated, different audio devices may output different levels of power to the speaker when connected thereto resulting in different output volumes. Accordingly, the volume control unit may prevent excessive speaker volume or allow adjustment of the volume of the speaker system to prevent excessive speaker volume. In one arrangement, the volume control unit includes a current limiting circuit that limits current that is received by the speaker. Accordingly, by limiting the current received by the speaker, the maximum output volume of the speaker may be capped. In another arrangement a power dissipating element such as an attenuator may be disposed between the plug and the speaker to limit speaker output. In such arrangements, it may be desirable that the speaker volume be limited to a safe range of about 90 dB.

In another arrangement, the volume control unit includes a manual volume control. Such a manual volume control may be attached directly to the speaker or disposed in a speaker wire between the speaker and the audio plug. Such a manual control allows the mother to independently and manually control the volume of sound and/or music being transmitted to the baby in the womb. Furthermore, the mother may use a separate headset attached to a dual universal audio plug attachment and listen to the same audio device, at the same time as the baby in the womb, while controlling the unborn baby's volume separately from her volume.

In one arrangement, the belt includes a second internal pocket that is sized to receive and house the speaker. Again this pocket may include means to securely close the pocket. In one arrangement, the second pocket is disposed within the first internal pocket. Use of such a second pocket allows for removing the speaker from the belt such that the belt may be cleansed.

DETAILED DESCRIPTION

Reference will now be made to the accompanying drawings. The description is not intended to limit the invention to the form and function disclosed herein. The function of the invention is for the purpose of delivering sounds and/or music to an unborn baby in the mother's womb. A user may also attach a separate headset (optional) to a dual audio plug attachment (optional) and listen to the same audio device at the same time. A volume control unit of the speaker allows a mother to limit the volume of sound received by the unborn baby.

Figure 5:
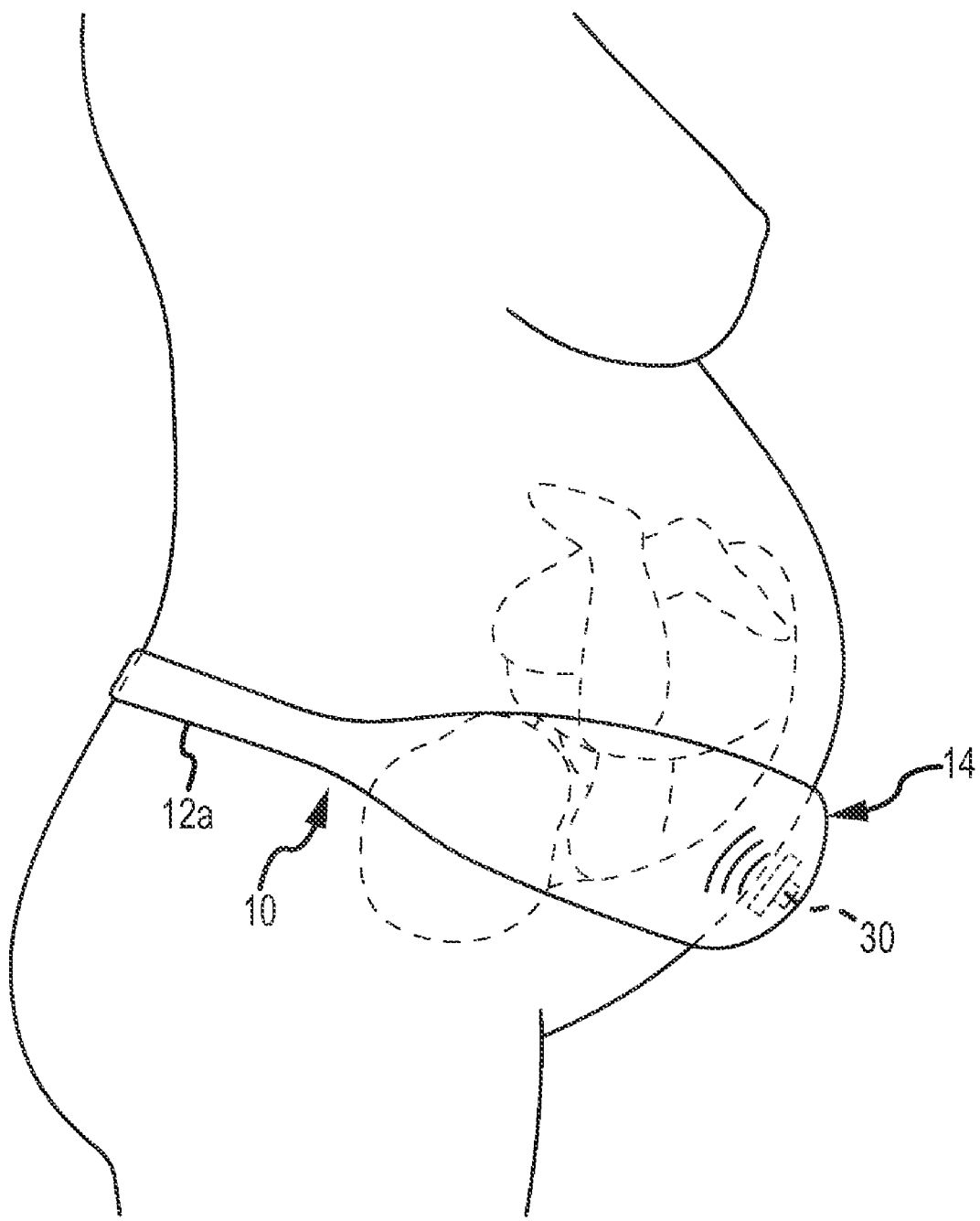
FIG. 5 is a drawing of an embodiment the prenatal sound/music as worn around the abdomen

Generally the device includes a size adjustable flexible abdominal belt 10 with elongated ends 12a, 12b (e.g., end straps) for securing around the abdomen of a user. The belt 10 is generally a thin soft pliable material with a front side and a back side that is secured together by stitching. Each layer of the belt may be a single piece of material that includes the elongated ends 12a, 12b with the mid-section 14 being slightly larger in width than the elongated end straps 12a, 12b. The elongated end straps 12a, 12b reach around the user's waist (see for example FIG. 5) which, in the present embodiment, secure together by hook and loop fasteners 16 stitched to each elongated strap by laying one strap on top of the other strap. The mid-section 14 houses a speaker 30 that may be connected to an audio device such as, for example, a CD player, MP3 player etc. As shown in FIG. 5, when the abdominal belt 10 is worn around the abdomen sound may be transmitted to the fetus in the mother's womb through the internally disposed speaker 30.

To use the invention, an expectant mother puts the abdominal belt 10 around her waist with the speaker 30 enclosed within the belt 10 facing inwards towards the unborn baby in the womb. The mother then secures the size adjustable belt 10 using connectors 16 on the end straps 12a, 12b of the belt. The mother then opens a built-in pocket 40 to retrieve a speaker cable 34 and plugs it into an appropriate portable audio playing device using a universal audio plug 36. If the user is utilizing a portable audio device, she can then place the portable audio device back in the internal pocket 40 for temporary storage while in use. The user has the ability to play any type of pre-recorded sounds and/or music from the audio device of her choosing, such as; a radio/stereo, digital audio device (i.e. an iPod® or other MP3 type players, MP3 player cell phones, or other digital media players), cassette player, CD player, portable radio, and the like. To limit the output of the speaker 30 a volume control unit 38 is disposed between the speaker and 30 and the audio plug 36.

Figure 2:
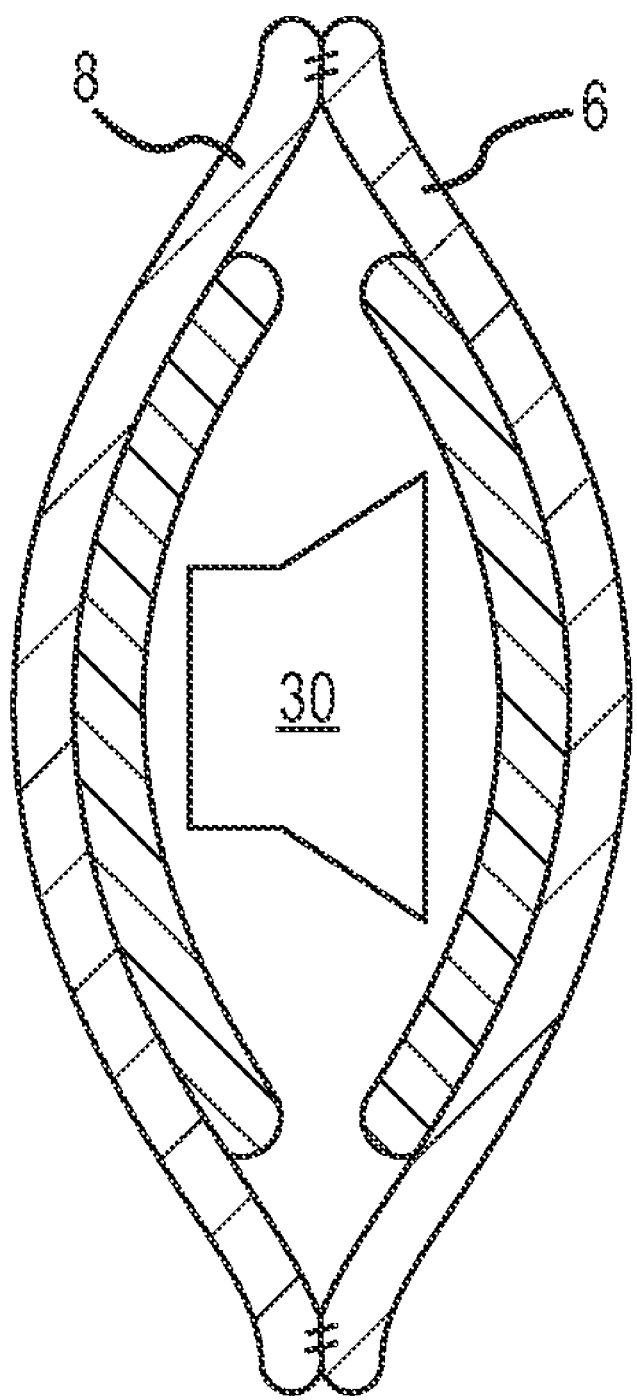
FIG. 2 is a drawing of a cross section of a portion of the belt of FIG. 1.

Generally, the waist belt 10 is comprised of multiple layers to provide a soft comfortable engagement with the abdomen of a user. When the inner layer 6 and outer layer 8 are stitched together, they enclose the internal closable pocket 40 there between. This internal pocket 40 may be made of additional thin soft pliable material and disposed in the mid section 14 of the belt 10. FIG. 2 illustrates a cross section of the speaker 30 disposed within the belt 10 as it transmits sound and/or music to the unborn baby in the mother's womb. The speaker 30 is surrounded by the internal cushioning 4 that is itself enclosed by the soft pliable inner and outer layers 6, 8. That is, the inner and outer layers of the belt, which are typically stitched together, may also enclose multiple layers of cushioning around the speaker 30.

Figure 1:
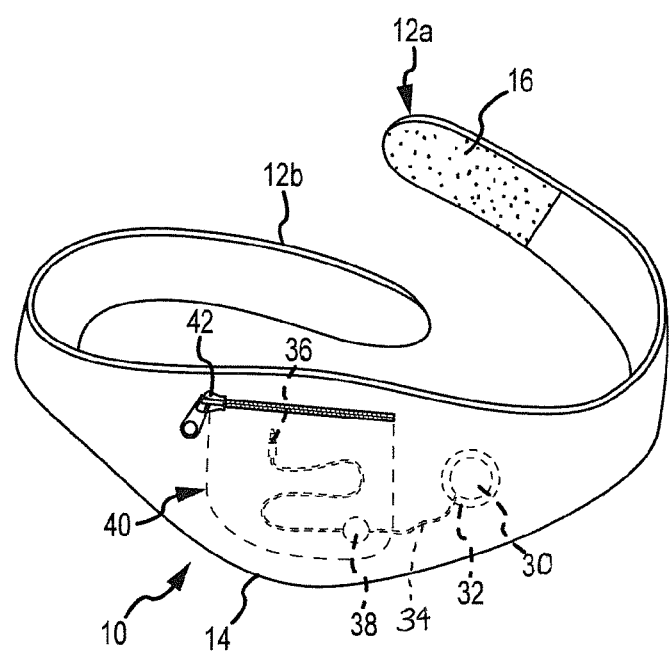
FIG. 1 is a drawing of one embodiment of a prenatal sound/music belt.

FIG. 1 illustrates a first embodiment of the abdominal belt 10 with the elongated end straps 12a, 12b that may be secured together by hook and loop fasteners 16. In this embodiment, the speaker is a built-in fixed speaker 30. In this embodiment, the speaker 30 may be sewn into a pouch 32 between the layers of the belt. That is, a seam may be sewn around the periphery of the speaker. A speaker cable 34 extends from the speaker 30 within the internal pouch and is fed through an eyelet into the internal pocket 40, which in the present embodiment includes a zipper 42 to selectively access the pocket 40. The universal audio plug 36 may then connect to an audio device. A portion of the speaker wire is fed through an eyelet in the internal pocket so the audio plug and volume control unit can be accessed by the user by reaching into the pocket to retrieve the cable and plug it into an audio device.

Figure 3:
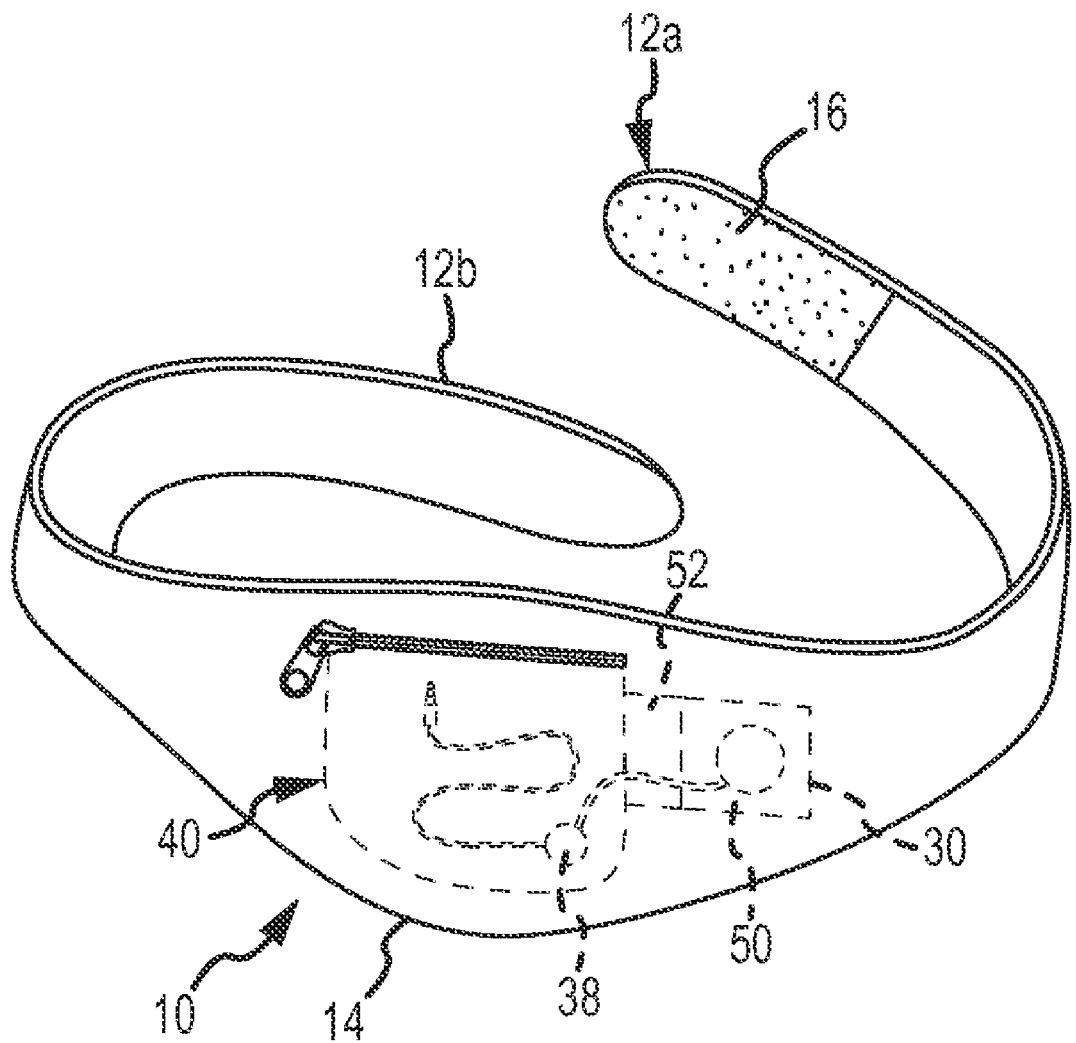
FIG. 3 is a drawing of a second embodiment of the prenatal sound/music belt.

FIG. 3 illustrates a second embodiment of the abdominal belt 10 with the elongated end straps 12a, 12b that may be secured together by hook and loop fasteners 16. In this embodiment, the speaker 30 is removeably received within the belt 10. That is, in this embodiment, the speaker 30 is received within a second internal pocket 50. As with the first internal pocket 40, this second internal pocket 50 may be made of additional thin soft pliable material and disposed within the mid section 14 of the belt 10. In this particular embodiment, the opening of the second pocket 50 opens into the first pocket 40. A hook and loop fastener 52 along the opening of the second internal pocket 50 allows for closing the pocket. Other fasteners (e.g., zippers) may be used as well. The speaker cable 34 extending from the speaker 30 within the second pocket passes through the opening of the second pocket into the first internal pocket 40. Again, this speaker cable includes a universal audio plug 36 for connection to an audio device. The second internal pocket 50 is generally sized to be substantially conformal with the speaker 30. In this regard, when the speaker 30 is disposed within the pocket 50 the speaker cannot easily turn over. Stated otherwise, the size of the second pocket 50 maintains the orientation of the speaker 30 toward the interior of the belt 10, which is disposed against the abdomen of a user when the belt is worn.

Figure 4A:
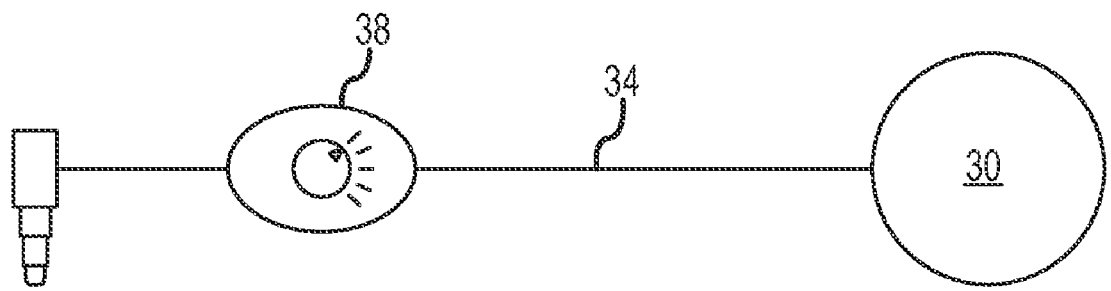
FIG. 4A is a drawing of a speaker including a first volume control unit.

FIG. 4A illustrates one embodiment of a speaker 30 with speaker wire/cable 34 extending between the speaker and the audio plug 36 where a volume control unit is disposed in-line between the speaker 30 and the audio plug. As shown, in the present embodiment, the volume control unit 38 is formed from a manually adjustable dial that adjusts the volume output of the connected speaker 30.

Figure 4B:
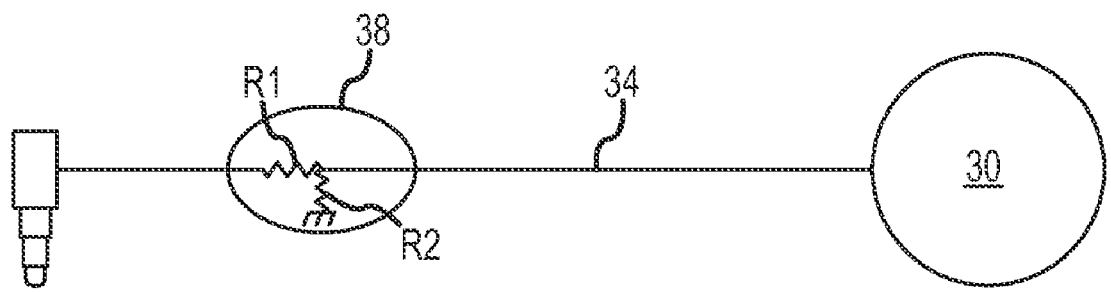
FIG. 4B is a drawing of a speaker including a second volume control unit.

FIG. 4B illustrates a second embodiment where the volume control unit is a passive electronic element (i.e., requiring no user interaction) that is disposed between the audio plug 36 and the speaker 30 to limit the sound pressure level of the speaker. That is, in this embodiment, the maximum sound pressure level (SPL) that can be reached when driven by an audio player is reduced. In most speaker applications, a speaker is driven directly by an audio device (Mp3 etc). Here, the volume control unit limits the amount of power delivered to the speaker 30 by inserting an energy dissipating device between the audio plug 36 and the speaker 30. Instead of all the power from the audio device going to the speaker 30, a designated percentage of the power is dissipated prior to reaching the speaker. As power to the speaker is reduced, so is the sound pressure, or, sound pressure level that is output by the speaker.

For example, typical earphones for headphones may produce over 100 dB of volume at the eardrum. It is recognized that exposure to over 90 dB can result in permanent hearing loss, depending on the combination of decibel level and duration of the exposure. It therefore may be desirable to limit the maximum output of the speaker to a safe range of about 90 dB. It will be appreciated that the maximum output level of a speaker is based at least in part on the electrical characteristics of a speaker including, without limitation, impedance ratings, Ohm ratings and watts.

Various passive electronic elements may be utilized to reduce the output amplitude (e.g., SPL) of a speaker. For instance, variously configured attenuator pads may be provided to form a volume control units. Such attenuator pads are often nothing more than a network made of resistors that creates loss (attenuation) in a transmission line (e.g., between the audio device and the speaker). Although there are many different configurations (V, L, T, bridged-T, etc.), they essentially all boil down to a form of a voltage divider. Two resistors in series, with the input across both, and the output across one. By selecting the configuration and the resistance of the resistors R1 and R2 based on the electrical characteristics (e.g., Ohms, imprudence, etc) of the speaker and expected drive voltage and/or current, an attenuator may be designed to produce a desired dB reduction to a speaker. That is, the maximum SPL output of the speaker may be reduced to a desired level. The embodiment in FIG. 4B utilizes an "L-pad", which is an attenuating device with two variable impedance pads. It has constant impedance with respect to the amplifier. The "L-Pad" provided minimal sound distortion due to minimal phase shift and provides very linear attenuation up to its power rating. However, it will be appreciated that the passive volume control is not limited to this exemplary embodiment.

The foregoing description has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. It is intended that the appended claims be construed to include alternative embodiments to the extent permitted by the prior art.

The invention claimed is:

1. A volume controlled prenatal sound and music belt providing additional safety, over any known device, for the developing baby's hearing comprising:
    a size adjustable flexible abdominal belt including a front and back layer secured together by stitching;
    a connector for connecting first and second ends of the belt;
    a first internal pocket disposed in a mid-portion of the belt between the front and back layers of the belt, said first internal pocket having a first opening for accessing the first internal pocket;
    a closing element for selectively securing the first opening of the first internal pocket;
    a speaker disposed within a pouch in said abdominal belt and facing toward the back layer, wherein the back layer is disposed against an abdomen of a user when said belt is worn;
    a signal cable extending within a space between the front and back layers from said speaker and ending in an electrical plug, wherein the signal cable extends from the speaker and into the first internal pocket free of exiting the space between the front and back layers, and wherein the electrical plug is adapted to be tucked into the first internal pocket so that the entirety of each of said signal cable and said electrical plug is disposable between the front and back layers of the belt when the electrical plug is engaged with an audio device; and
    a volume control unit for controlling the volume of sound being transmitted by said speaker when said electrical plug is engaged with the audio device, wherein said volume control unit operates independent of the volume transmitted by such an audio device, wherein said volume control unit is disposed on said signal cable in-line between said speaker and said electrical plug, and wherein said volume control unit comprises an electronic circuit for limiting a magnitude of a signal received from said audio device.

2. The apparatus of claim 1, wherein said volume control unit comprises:
    a manual volume control.

3. The apparatus of claim 1, wherein said electronic circuit comprises a gain control circuit.

4. The apparatus of claim 1, wherein said electronic circuit comprises a current limiting circuit.

5. The apparatus of claim 1, wherein said electronic circuit comprises a power dissipating element.

6. The apparatus of claim 1, wherein said speaker is fixedly sewn into said belt between said first and second layers, wherein said signal cable extends through an eyelet into said first internal pocket.

7. The apparatus of claim 1, further comprising:
    a second internal pocket sized to receive said speaker.

8. The apparatus of claim 7, wherein said second internal pocket comprises a second opening for accessing the second pocket.

9. The apparatus of claim 8, wherein said second opening opens into said first internal pocket.

10. The apparatus of claim 9, further comprising:
    a hook and loop connector for selectively closing said second opening.

11. The apparatus of claim 9, wherein said volume control unit limits the output of said speaker to an upper range of about 90 dB.

12. A volume controlled prenatal sound and music belt providing additional safety, over any known device, for the developing baby's hearing comprising:
    a size adjustable flexible abdominal belt including a front and back layer secured together by stitching;
    a connector for connecting first and second ends of the belt;
    a first internal pocket disposed in a mid-portion of the belt between the front and back layers of the belt, said first internal pocket having a first opening for accessing the first internal pocket;
    a first closing element for selectively securing the first opening of the first internal pocket;
    a second internal pocket disposed in the mid-portion of the belt between the front and back layers of the belt, the second internal pocket having a second internal opening for accessing the second internal pocket, wherein the second internal opening opens directly into the first internal pocket;
    a second closing element for selectively securing the second internal opening of the second internal pocket;
    a speaker disposed within the second internal pocket of said abdominal belt, wherein the second internal pocket is sized to hold the speaker facing toward the back layer, wherein the back layer is disposed against an abdomen of a user when said belt is worn;
    a signal cable extending from said speaker and ending in an electrical plug, wherein the signal cable extends from the speaker through the second internal opening and into the first internal pocket; and
    a volume control unit for controlling the volume of sound being transmitted by said speaker when said electrical plug is engaged with an audio device, wherein said volume control unit operates independent of the volume transmitted by such an audio device.

13. The apparatus of claim 12, wherein said volume control unit comprises:
    a manual volume control.

14. The apparatus of claim 12, wherein said volume control unit is disposed in-line between said speaker and said electrical plug.

15. The apparatus of claim 12, wherein said volume control unit comprises:
    an electronic circuit for limiting a magnitude of a signal received from said audio device.

16. The apparatus of claim 12, wherein the volume control unit limits the output of the speaker to an upper range of about 90 dB.

17. The apparatus of claim 12, wherein the width of the mid-portion is greater than the width of the first and second ends of the belt.

* * * * *